United States Patent [19]

Satake et al.

[11] Patent Number: 5,034,609
[45] Date of Patent: * Jul. 23, 1991

[54] METHOD FOR EVALUATING QUALITY OF RAW COFFEE BEANS

[75] Inventors: Toshihiko Satake, Hiroshima; Satoru Satake, Tokyo; Yukio Hosaka, Hiroshima, all of Japan

[73] Assignee: Satake Engineering Co., Ltd., Tokyo, Japan

[*] Notice: The portion of the term of this patent subsequent to Oct. 16, 2007 has been disclaimed.

[21] Appl. No.: 565,235

[22] Filed: Aug. 10, 1990

Related U.S. Application Data

[62] Division of Ser. No. 421,849, Oct. 16, 1989, Pat. No. 4,963,743.

[30] Foreign Application Priority Data

Oct. 15, 1988 [JP] Japan ................................ 63-260315
Oct. 29, 1988 [JP] Japan ................................ 63-274269

[51] Int. Cl.⁵ ............................................ G01N 21/35
[52] U.S. Cl. .................................. 250/339; 250/341; 250/343
[58] Field of Search ........................ 250/339, 341, 343

[56] References Cited

U.S. PATENT DOCUMENTS

| | | | |
|---|---|---|---|
| 3,686,384 | 8/1972 | Runton | 264/122 |
| 3,776,642 | 12/1975 | Anson et al. | 250/339 |
| 4,260,262 | 4/1981 | Webster | 250/339 |
| 4,633,087 | 12/1986 | Rosenthal et al. | 250/341 |
| 4,742,228 | 5/1988 | Bischoff | 250/359.1 |
| 4,752,689 | 6/1988 | Satake | 250/339 |
| 4,800,280 | 1/1989 | Satake | 250/339 |
| 4,806,764 | 2/1989 | Satake | 250/339 |

OTHER PUBLICATIONS

"Characteristics of Non-Destructive Near-IR Instruments for Grain & Food Products," Robert D. Rosenthal.

Primary Examiner—Constantine Hannaher
Assistant Examiner—Drew A. Dunn
Attorney, Agent, or Firm—Wegner, Cantor, Mueller & Player

[57] ABSTRACT

In an apparatus for evaluating raw coffee beans, a near-infrared light beam is applied to sample coffee powder, and a detector receives light reflected from and/or transmitted through the sample coffee powder to generate a signal representative of luminous intensity of the received light. A memory device has stored therein at least one of characteristic coefficients and appraisal coefficients for the sample coffee powder. A calculation device calculates at least one of characteristic values and appraisal values of the raw coffee beans; based on the stored coefficients and the signal from the detector.

16 Claims, 10 Drawing Sheets

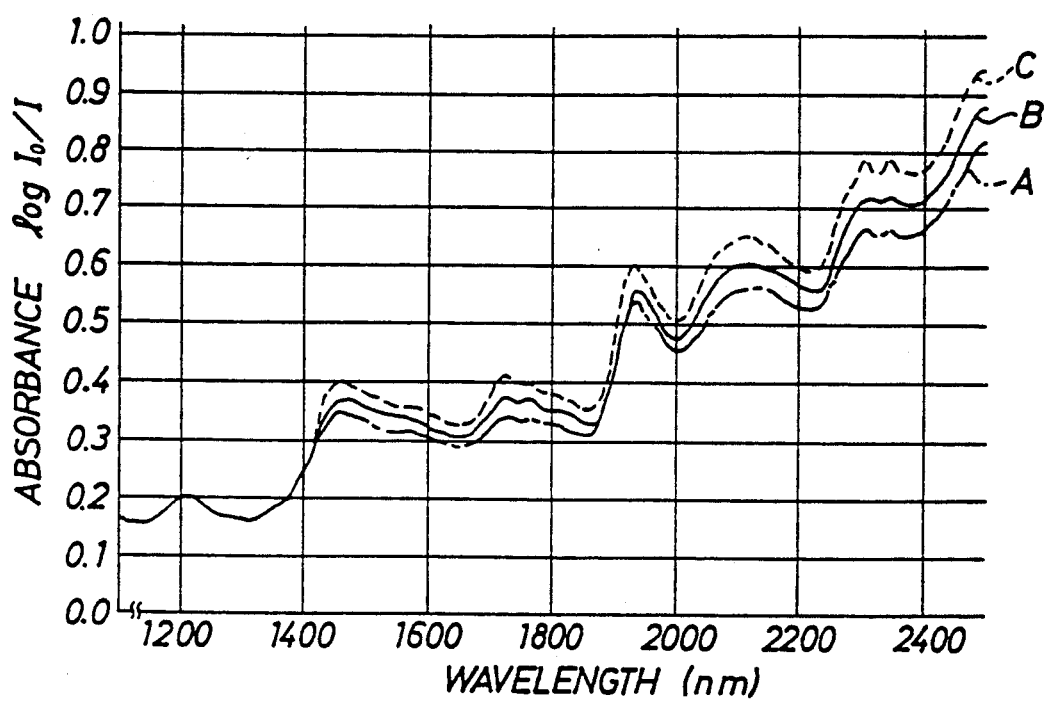

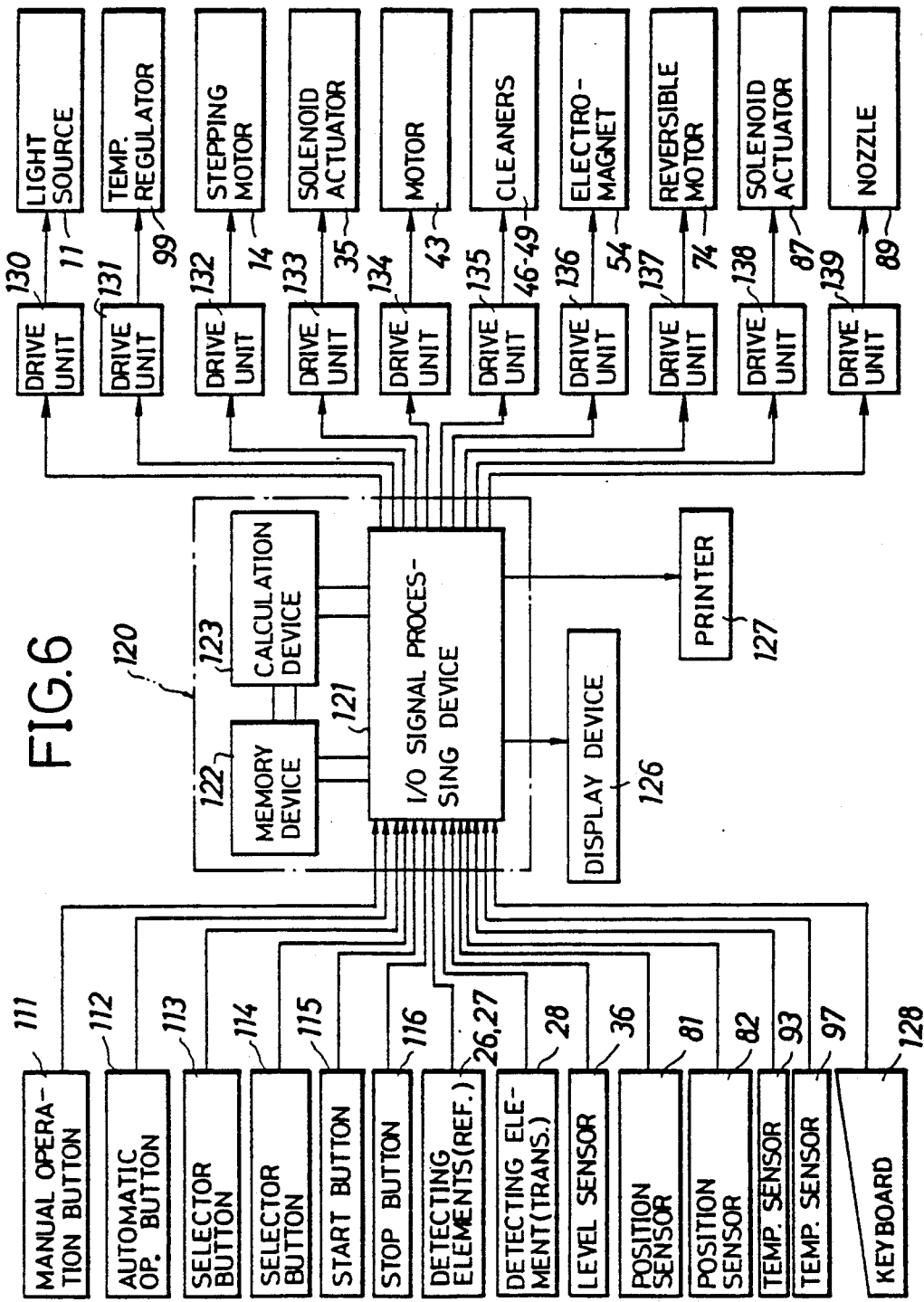

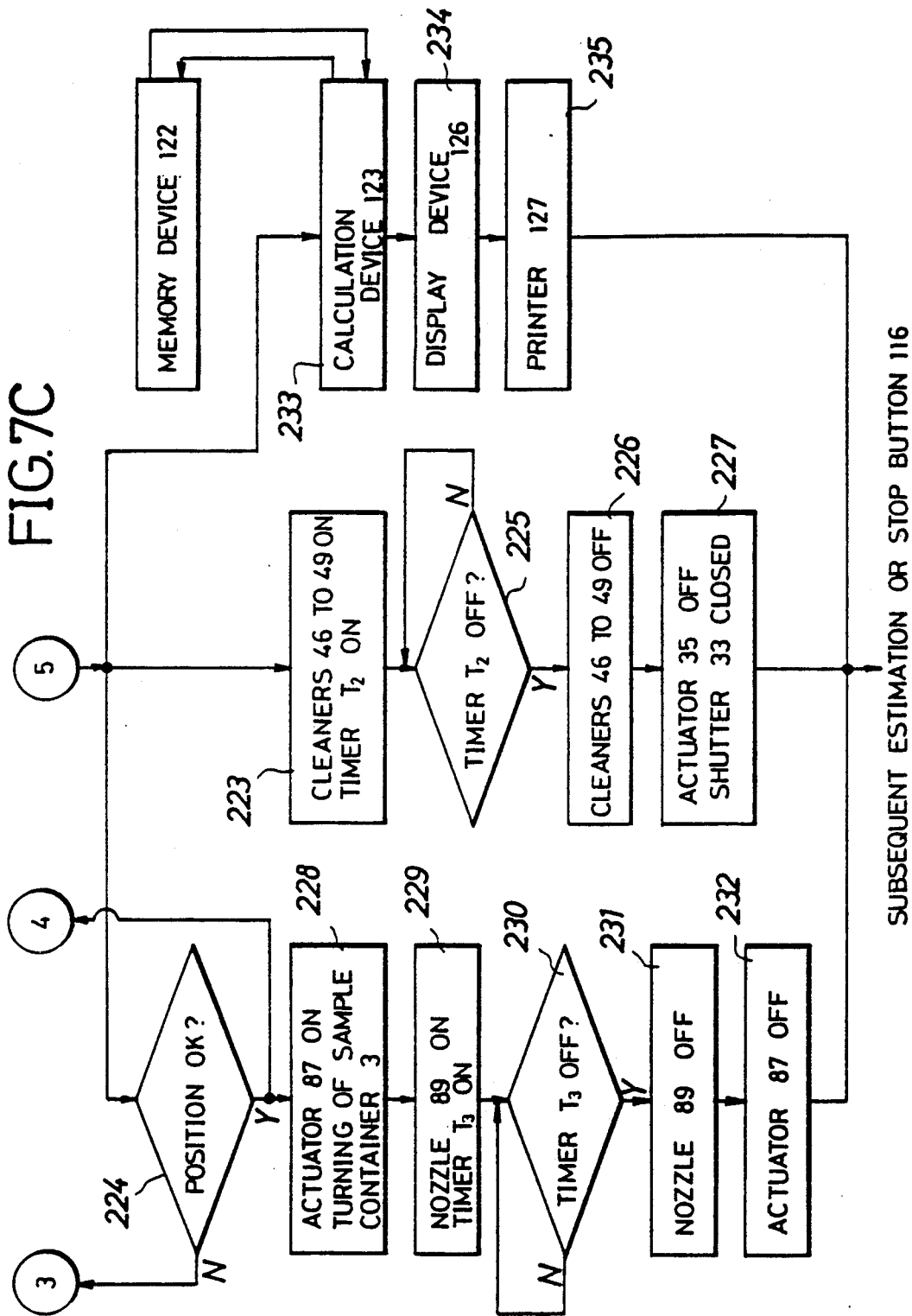

METHOD FOR EVALUATING QUALITY OF RAW COFFEE BEANS

CROSS REFERENCE TO RELATED APPLICATIONS

This application is a division of Ser. No. 07/421,849, filed Oct. 16, 1989, now U.S. Pat. No. 4,963,743 issued Oct. 16, 1990.

The invention is concerned with U.S. Ser. No. 24,139 (U.S. Pat. No. 4,752,689) entitled "Apparatus For Evaluating The Quality Of Rice Grains" filed on Mar. 10, 1987 in the name of Toshihiko SATAKE assigned to the assignee of this invention, and U.S. Ser. No. 97,748 (U.S. Pat. No. 4,800,280) entitled "MEASURING APPARATUS FOR AMYLOSE AND/OR AMYLOPECTIN CONTENT IN RICE" filed on Sept. 17, 1987 in the name of Toshihiko SATAKE assigned to the assignee of this invention.

BACKGROUND OF THE INVENTION

The present invention relates to an apparatus for evaluating quality of coffee beans, particularly, raw coffee beans.

A coffee berry is called a "cherry" at the another name, and has a fleshy or pulpy husk on the outside and a sarcocarp on the inside. Further, the coffee berry has an endocarp and a silver skin, and an albumen at the extremely center point. Raw coffee beans generally circulated under commercial transactions are those from which slight parts of the endocarp and the silver skin are removed slightly, and moisture content of the raw coffee beans is 13% to 15%. The raw coffee beans are high or strong in viscosity and elasticity, and it is difficult to pulverize the raw coffee beans uniformly.

Generally available coffee beans are those in which flesh is removed from a completely ripe coffee fruit and in which dried and chosen seeds (raw coffee beans) are roasted. It is said that a taste of coffee such as acidity, bitterness and smell or aroma depends upon difference in condition of the roasting. On the other hand, however, it is also known that considerable difference in taste is caused by the quality of raw coffee beans due to difference in kind and cultivation of the coffee. That is, taste and flavor of the coffee are primarily decided by difference in quality and roasting condition of the raw beans, but if the roasting condition is the same, the taste of coffee is substantially decided by the quality of raw beans.

By the way, conventionally, judgment on the taste of coffee is based on a so-called sensuous examination in which roasted beans are pulverized, hot water is added to the pulverized beans, and operators actually taste the water. Accordingly, a plurality of operators and a long time are required for doing full justice to the judgment. Further, since the judgment is effected on the basis of the palate or taste having individual difference, it is difficult to say that the judgment is effective and unchangeable.

It is also conducted that caffeine is drawn out of roasted coffee beans, and content of the caffeine is measured chemically. This is not evaluation of the quality per se of the coffee beans.

In summary, it is the present condition that no trial or attempt is made to carry out measurement or evaluation at the stage of raw coffee beans.

Below table indicates scientific measurement and analysis of chemical components of raw coffee beans and roasted coffee beans.

TABLE

| | PRO-TEIN | CANE SUGAR | (%) CHLOROGENIC ACID |
|---|---|---|---|
| RAW BEANS | 11.6 | 7.3 | 7.6 |
| ROASTED BEANS | 3.1 | 0.3 | 3.5 |

| CAFFEINE | TRIGONELLINE | RESIN | REDUCING SUGAR |
|---|---|---|---|
| 1.2 | 1.1 | 11.4 | 0.7 |
| 1.3 | 0.7 | 11.9 | 0.5 |

| HEMI-CELLULOSE | CELLULOSE | LIGNIN | UNKNOWN COMPONENT |
|---|---|---|---|
| 23.0 | 12.7 | 5.6 | 14.0 |
| 24.0 | 13.2 | 5.6 | 31.7 |

According to the above table, it is understood that components considerably reduced after having been roasted are protein, cane sugar and chlorogenic acid. It is considered that these three components are primary elements which create taste and flavor by heat reaction at the time of roasting.

SUMMARY OF THE INVENTION

It is an object of the invention to provide an apparatus for evaluating quality of raw coffee beans, which can measure content of at least one component contained in the raw coffee beans for a short period of time, thereby obtaining an objective-quality estimating value of the raw coffee beans.

According to the invention, there is provided an apparatus for evaluating quality of raw coffee beans, characterized by comprising:

pulverizing means for pulverizing the raw coffee beans to form sample coffee powder;

a sample container located at a predetermined measuring position with the sample coffee powder to be evaluated being contained in said sample container;

a near-infrared spectrometer including a light source for applying light to said sample coffee powder, optical means located between said light source and said sample coffee powder for permitting passage of near-infrared light beam having its specific wavelength, of the light from said light source, and luminous-intensity detecting means for detecting luminous intensity of the light reflected from and/or transmitted through said sample coffee powder to generate a signal representative of the luminous intensity; and control means including memory means for storing therein at least one of characteristic coefficients and appraisal coefficients for said sample coffee powder, and calculation means for calculating at least one of characteristic values and appraisal values of said raw coffee beans, based on said stored coefficients and said signal from said luminous-intensity detecting means.

According to the evaluation apparatus of the invention, it is not necessary to depend upon sensuous examination due to the palate or taste of an operator, which has individual difference, a chemical quantitative analysis which requires considerable skill, or the like. Anyone can obtain the accurate appraisal value of the sample coffee powder easily and for a short period of time.

Preferably, the pulverizing means includes a perforated member and a plurality of blade means rotatable for scattering and blowing off the coarse powder against the perforated member to cause the sample coffee powder to pass through perforations of the perforated member thereby forming the sample coffee powder. Thus, the sample coffee powder can be uniformized in grain or particle size and can be averaged in distribution of the grain size.

BRIEF DESCRIPTION OF THE DRAWINGS

FIG. 3 is a graph of absorbance curves showing the relationship between the wavelengths of near-infrared light beam and the absorbance with respect to various coffee beans;

FIG. 6 is a block diagram of a control unit incorporated in the evaluating apparatus shown in FIG. 1;

FIGS. 7A through 7C are a flow chart showing the operation of the evaluating apparatus illustrated in FIG. 1;

DETAILED DESCRIPTION

The invention will now be described, by way of mere examples, with reference to the accompanying drawings.

Figure 1:
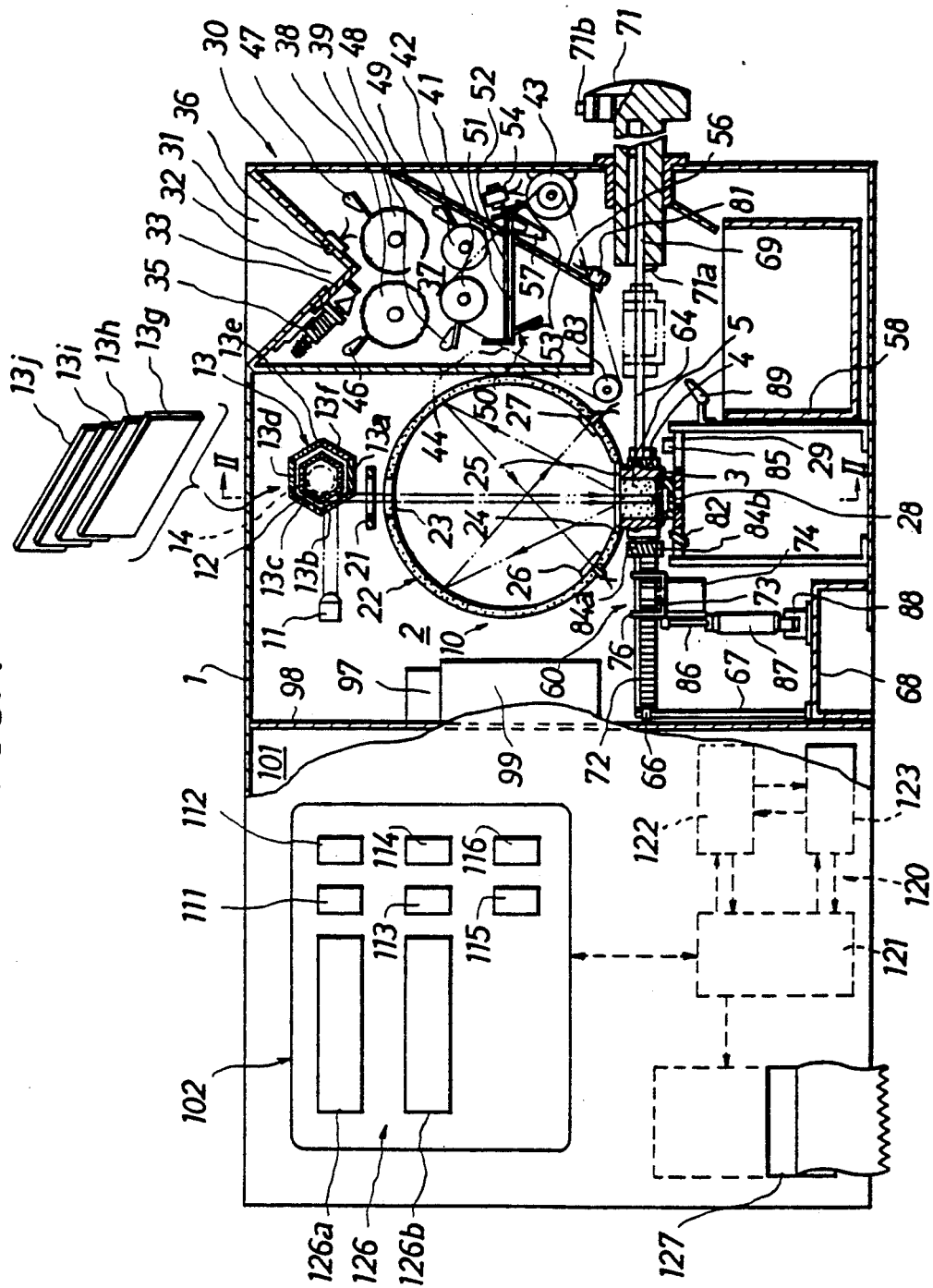
FIG. 1 is a partially broken-away, front elevational view of an apparatus for evaluating quality of raw coffee beans, according to an embodiment of the invention.

Referring first to FIG. 1, there is schematically illustrated an apparatus for evaluating quality of raw coffee beans, according to an embodiment of the invention. The evaluating apparatus comprises a cabinet 1 generally in the form of a rectangular parallelepiped, which defines therein a measuring chamber 2. A sample container 3 having a transparent bottom wall is held by a holder 4 at a predetermined measuring position in a lower portion of the measuring chamber 2. The sample container 3 has received therein sample coffee powder 5 to be evaluated which has been ground or pulverized to have a particle size equal to or less than 500 $\mu$m, preferably, of approximately 50 $\mu$m. A predetermined or constant amount of sample coffee powder 5 is arranged to be filled in the sample container 3.

Figure 2:
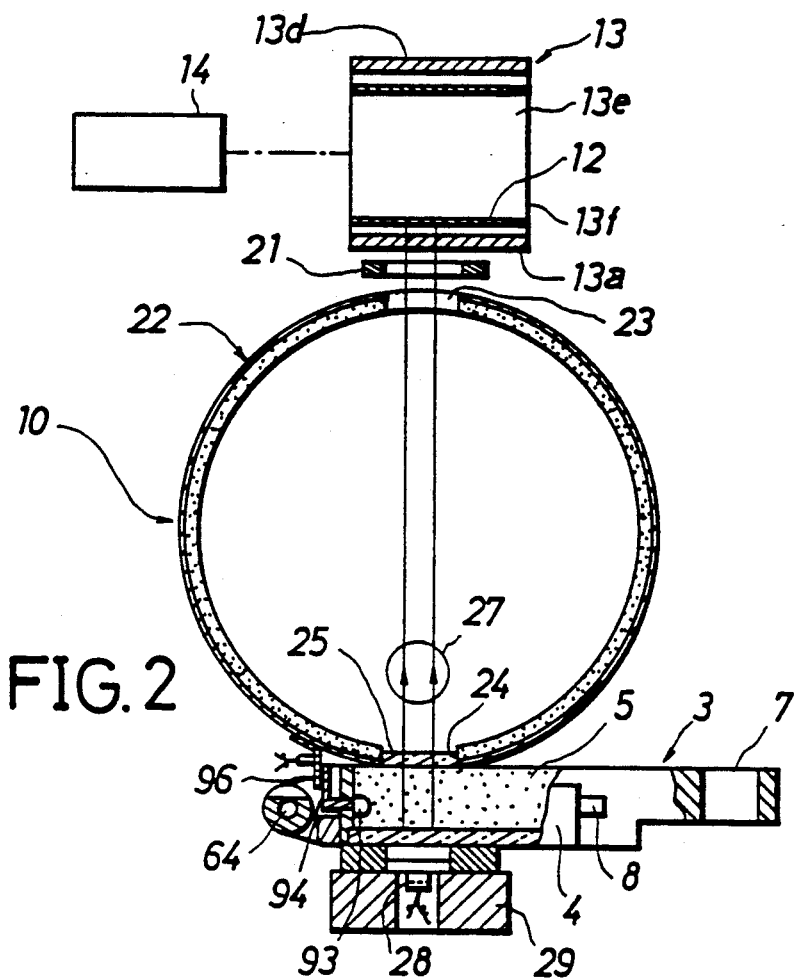
FIG. 2 is an enlarged cross-sectional view taken along the line II—II in FIG. 1, showing in detail a near-infrared spectrometer illustrated in FIG. 1.

Incorporated in the measuring chamber 2 is a near-infrared spectrometer generally designated by the reference numeral 10 in FIGS. 1 and 2. The near-infrared spectrometer 10 comprises a light source 11, such as a halogen lamp, which is mounted to a rear wall of the cabinet 1 in an upper portion of the measuring chamber 2. A hexagonal reflecting mirror 12 is so positioned with respect to the light source 11 as to reflect the light from the light source 11 to any desired direction. An optical filter assembly 13 constituting optical means is drivingly connected to a stepping motor 14 mounted to the rear wall of the cabinet 1. The optical filter assembly 13 is composed of six optical filters 13a to 13f which are replaceable and which are arranged in the form of a regular hexagon about the reflecting mirror 12. The optical filter assembly 13 further has another four filters 13g through 13j which are prepared separately and each of which can be mounted to the body of the filter assembly 13 in substitution for any one of the filters 13a to 13f. The ten filters 13a through 13j have their respective wavelength bands which are within a range of from 1100 nm to 2500 nm.

The optical filter assembly 13 is angularly moved stepwise by the stepping motor 14 by a predetermined angle so that selected one of the six and four optical filters 13a to 13f and 13g to 13j can be aligned with the optical axis of the light from the light source 11, and so that it is possible to optionally adjust a crossing angle between the face of the selected optical filter and the optical axis of the light from the light source 11.

For example, first one 13a of the optical filters has its nominal wavelength of approximately 1680 nm; second one 13b, approximately 1818 nm; third one 13c, approximately 1840 nm; fourth one 13d, approximately 1904 nm; fifth one 13e, approximately 1940 nm; sixth one 13f, approximately 2100 nm; seventh one 13g, approximately 2180 nm; eighth one 13h, approximately 2190 nm; ninth one 13i, approximately 2230 nm; and tenth one 13j, 2310 nm. A "nominal wavelength" is the maximum passing wavelength of the near-infrared light beam which passes through an optical filter when the optical axis of the incident light beam is at right angles to the face of the optical filter.

The physical properties required for the optical filters 13a to 13j will now be described with reference to FIG. 3 which is a graph of absorbance curves showing the relationship between the wavelengths of illuminating light beam and the absorbance at the time when the near-infrared light beam whose wavelength is continuously varied is applied to different sample coffee beans. What is "absorbance" is the common logarithm of the reference luminous intensity (entire luminous intensity) $I_O$ of the illuminating light beam to the luminous intensity I of the light beam reflected from or transmitted through the sample coffee beans, that is log $I_O/I$. The curves A, B and C indicated respectively by the solid, dotted and broken lines represent various coffee beans. It will readily be seen from FIG. 3 that the short wavelength of near-infrared light below 1100 nm is a region of low absorbance in which there are only slight differences in the absorbance, and with the 1100 nm as a dividing line, the long wavelength of the near infrared from equal to or above 1100 nm to equal to or below 2500 nm is a region of high absorbance in which marked differences in the absorbance are noted with differences in contents of various components of the sample coffee beans. The present invention utilizes this phenomenon or these properties to evaluate the quality of raw coffee beans.

Referring back to FIGS. 1 and 2, the near-infrared spectrometer 10 further comprises a slit member 21 located below the optical filter assembly 13, and an integrating sphere 22 located below the slit member 21. The integrating sphere 22 is provided with a light intake window 23 opening at the slit member 21, and a measuring window 24 located in diametrically opposite relation to the light intake window 23 and opening at the aforesaid measuring position. The measuring window 24 is sealingly closed by a transparent plate 25 such as silical glass or the like to prevent dirt or dust from entering the integrating sphere 22. A pair of luminous-intensity detecting elements 26 and 27 are fixedly arranged within the integrating sphere 22 at respective positions symmetric to each other with respect to the measuring window 24. A further luminous-intensity detecting element 28 is fixedly supported at the measuring position on a support rod 29.

The light from the light source 11 becomes a near-infrared monochromatic light beam having specific wavelength after having passed through a selected one of the six and four optical filters 13a to 13f and 13g to 13j, and enters the integrating sphere 22 through the light intake window 23 thereof. The near-infrared monochromatic light beam having entered the integrating sphere 22 is applied vertically to the sample coffee powder 5 within the sample container 3 through the transparent plate 25 which closes the measuring window 24. A part of the light having entered the integrating sphere 22 is reflected from the sample coffee powder 5, is then reflected from the inner wall surface of the integrating sphere 22, and finally reaches the pair of luminous-intensity detecting elements 26 and 27. Thus, the luminous intensity of the reflected light is detected by the elements 26 and 27. In addition, the remaining part of the light having entered the integrating sphere 22 is transmitted through the sample coffee powder 5 and the transparent bottom wall of the sample container 3, and reaches the luminous-intensity detecting element 28. Thus, the luminous intensity of the transmitted light is detected by the element 28.

As illustrated in FIG. 1, a sample supply mechanism, generally indicated by the reference numeral 30, is incorporated in the right-hand end of the cabinet 1. The sample supply mechanism 30 comprises a hopper 31 mounted to an upper portion of the right-hand end of the cabinet 1. The hopper 31 is provided at its bottom with a discharge port 32 which is adapted to be opened and closed by a slidable shutter 33. A solenoid actuator 35 mounted to the side wall of the hopper 31 is connected to the shutter 33 to slide the same for opening and closing the discharge port 32. A level sensor 36 is attached to the side wall of the hopper 31, for detecting the level of raw coffee beans to be pulverized or ground, which are received in the hopper 31.

Pulverizing means is arranged in a pulverizing chamber 37 below the discharge port 32. The pulverizing means includes a first pair of coarse grinding rollers 38 and 39 rotatable about their respective rotary axes spaced in parallel relation to each other. Each of the rollers 38 and 39 has a roughened circumferential surface. The pulverizing means further includes a second pair of fine grinding rollers 41 and 42 rotatably arranged below the first pair of coarse grinding rollers 38 and 39. The second pair of fine grinding rollers 41 and 42 have their respective axes spaced in parallel relation to each other, and each roller 41, 42 has a smooth circuferential surface.

The roller 38 of the first pair of coarse rollers is drivingly connected to the roller 41 of the second pair of fine rollers by means of gears, belt or the like. The roller 41 of the second pair of fine rollers is drivingly connected to a motor 43 fixedly mounted to the side wall of the cabinet 1, through a belt 44. Thus, when the roller 41 of the second pair of fine rollers is rotated by the motor 43, the roller 38 of the first pair of coarse rollers drivingly connected to the roller 41 is also rotated. When rotated, the first pair of coarse grinding rollers 38 and 39 coarsely pulverize the raw coffee beans supplied to the nip therebetween through the discharge port 32 of the hopper 31. Preferably, endocarps are removed from the raw coffee beans, and the raw coffee beans are supplied to the nip between the first pair of coarse grinding rollers 38 and 39. The coffee beans are dried to have moisture content of approximately 10% or below. When rotated, the second pair of fine grinding rollers 41 and 42 finely pulverize the pulverized coffee beans supplied to the nip therebetween through the nip between the first pair of coarse rollers 38 and 39. That is, the pulverized coffee beans are pulverized to below 500 $\mu$m by the rollers 41 and 42.

The rollers 38, 39, 41 and 42 have associated therewith respective cleaning devices 46, 47, 48 and 49 each of which is composed of a nozzle having an electromagnetic valve for blowing compressed air against the circumferential surface of a corresponding one of the rollers and a blade which is formed of elastic material and which is in sliding contact with the corresponding roller.

A vibratory screening device 50 is arranged below the second pair of fine grinding rollers 41 and 42, and comprises a vibratory frame 51 and a screen 52 mounted thereto and having meshes through which the sample coffee powder 5 below 500 $\mu$m can pass, preferably, meshes through which the sample coffee powder 5 below 50 $\mu$m can pass. The vibratory frame 51 is mounted to the side wall of the cabinet 1 through two leaf springs 53 and 53. The vibratory frame 51 has an upstanding end wall toward which an electromagnet 54 is disposed to face. When energized, the electromagnet 54 oscillates the vibratory frame 51 and the screen 52 mounted thereto. Powder of the raw coffee beans pulverized by the second pair of fine grinding rollers 41 and 42 falls onto the screen 52. Sample coffee powder to be evaluated having a desired particle size, which has passed through the meshes of the screen 52, is fed to a predetermined filling position by a guide chute 56 mounted to the side wall of the cabinet 1. Coffee powder remaining on the screen 52 passes through a discharge chute 57 attached to the vibratory frame 51, and is received in a container 58 which is capable of being taken in and out through a front wall of the measuring chamber 2.

Figure 4:
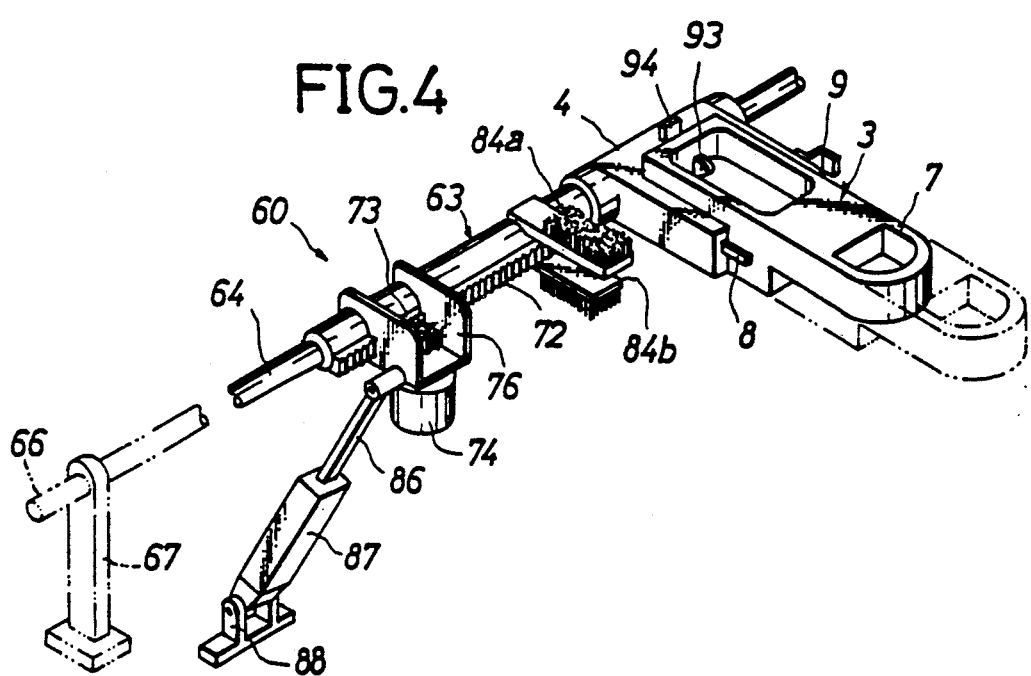
FIG. 4 is a perspective view of transport means illustrated in FIG. 1 for reciprocating a sample container between a filling position and a measuring position.

The aforementioned sample container 3 detachably held by the holder 4 is provided with a grip 7 as shown in FIG. 4. The holder 4 is generally in the form of the letter U, and has two legs formed respectively with guide grooves. On the other hand, the opposite sides of the sample container 3 are formed respectively with elongated projections 8 which are frictionally fitted respectively in the guide grooves. Thus, the sample container 3 can be detachably held by the holder 4.

The holder 4 is movable between the aforesaid measuring and filling positions by transport means generally designated by the reference numeral 60 in FIGS. 1 and 4. The transport means 60 comprises a hollow carriage 63 as shown in FIG. 4. The holder 4 is mounted on the carriage 63 for angular movement therewith about an axis of a guide rail 64 on which the hollow carriage 63 is mounted. The guide rail 64 has a circular cross-section, and the carriage 63 is slidable along the guide rail 64. The guide rail 64 has one end 66 thereof which is supported by a support leg 67 mounted on a table 68 which is in turn fixed to the bottom wall of the cabinet 1, as shown in FIG. 1. The other end 69 of the guide rail 64 is fitted in a manual turning handle 71 in such a manner that the guide rail 64 is angularly movable about its axis, together with the turning handle 71, but the turning handle 71 is axially movable along the guide rail 64.

The manual turning handle 71 is rotatably and slidably mounted through the side wall of the cabinet 1. The turning handle 71 has its distal end provided with a latch 71a which is operated by a push button 71b at the proximal end of the turning handle 71. The latch 71a is engageable with a hook 9 (see FIG. 4) provided on the leg of the holder 4.

Referring to FIG. 4, the carriage 63 is integrally formed with a rack 72 extending along the axis of the carriage 63. A pinion 73 in mesh with the rack 72 is fixedly mounted on an output shaft of a reversible motor 74. The motor 74 is attached to a bracket 76 which is mounted to the carriage 63 in such a manner that the bracket 76 is angularly movable together with the carriage 63 about the axis of the guide rail 64, but the carriage 63 is axially movable with respect to the bracket 76. When the motor 74 is energized, the pinion 73 in mesh with the rack 72 is rotated so that the carriage 63 is reciprocated along the guide rail 64. Thus, the holder 4 secured to the carriage 63 is capable of being reciprocated between the filling position, indicated by the double dotted lines in FIG. 1, where the sample coffee powder falling along the guide chute 56 is filled in the sample container 3, and the measuring position where the sample container 3 is located at the measuring window 24 of the integrating sphere 22.

Figure 5:
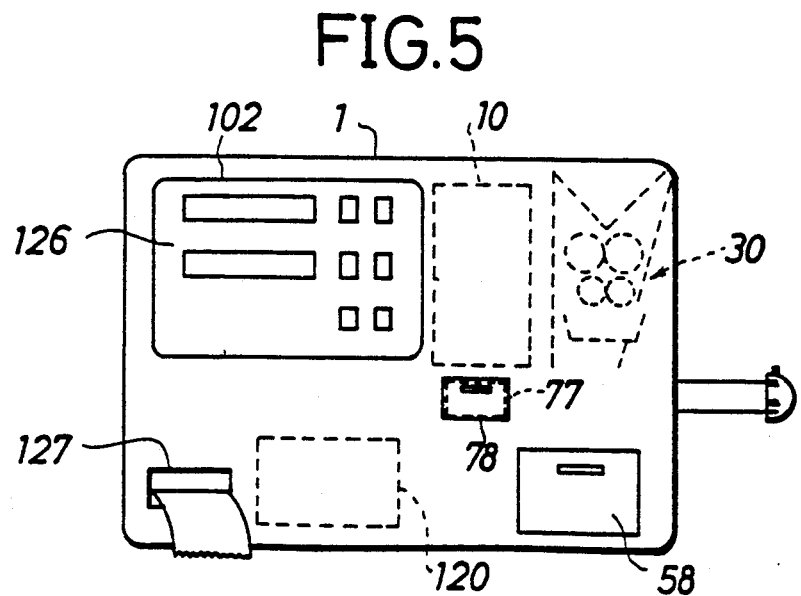
FIG. 5 is a front elevational view of the evaluating apparatus shown in FIG. 1.

As shown in FIG. 5, the front wall of the cabinet 1 is provided with an opening 77 closable by a cover 78. The sample container 3 may be filled with the sample coffee powder 5 which has been pulverized by an external pulverizing equipment separate from the grinding rollers 38, 39, 41 and 42 of the aforementioned sample supply mechanism 30, to be described later.

As illustrated in FIG. 1, a position sensor 81 attached to the guide chute 56 detects whether or not the holder 4 is located at the filling position, to generate a signal. A position sensor 82 secured to the support rod 29 having attached thereto the luminous-intensity detecting element 28 detects whether or not the holder 4 is located at the predetermined measuring position, to generate a signal. When the holder 4 moves from the filling position to the measuring position, a roller 83 rotated by the motor 43 through the belt 44 is brought into rolling contact with the top of the sample container 3 held by the holder 4 to compressively fill the sample coffee powder 5 into the sample container 3, and to remove excessive sample coffee powder from the sample container 3.

Moreover, as shown in FIG. 4, first and second cleaners 84a and 84b formed by synthetic resinous brushes or the like are secured to the carriage 63 adjacent the holder 4. When the holder 4 is moved between the filling and measuring positions, the first and second cleaners 84a and 84b are brought respectively into sliding contact with the lower surface of the transparent plate 25 closing the measuring window 24 of the integrating sphere 22 and the surface of the luminous-intensity detecting element 28, to respectively clean the plate 25 and the element 28. Furthermore, as illustrated in FIG. 1, a third cleaner 85 similar in construction to the first and second cleaners 84a and 84b is fixedly mounted to the aforesaid support rod 29 on which the luminous-intensity detecting element 28 is fixedly supported. When the holder 4 is moved between the filling and measuring positions, the lower surface of the transparent bottom wall of the sample container 3 is brought into sliding contact with the third cleaner 85, whereby the transparent bottom wall is cleaned.

As clearly shown in FIGS. 1 and 4, a telescopic rod 86 of a solenoid actuator 87 constituting turning means has a forward end pivotally connected to the bracket 76 on which the reversible motor 74 is mounted. The actuator 87 is pivotally supported by a pivot stand 88 secured to the table 68 shown in FIG. 1. When the solenoid actuator 87 is energized, the rod 86 is withdrawn to angularly move the bracket 76, hence, the carriage 63 by 90° about the axis of the guide rail 64. Thus, as the actuator 87 is energized when the holder 4 occupies the filling position, the sample container 3 held by the holder 4 is angularly moved through 90° about the axis of the guide rail 64, thereby permitting the sample coffee powder 5 to freely fall from the sample container 3. A nozzle 89 provided adjacent the filling position, as illustrated in FIG. 1, is arranged to blow compressed air against the sample container 3 after the latter has been angularly moved by 90°, to blow off the sample coffee powder 5 from the sample container 3, to thereby clean the interior thereof.

As clearly shown in FIG. 2, a temperature sensor 93 such as a thermistor is attached to the sample container 3 to detect temperature of the sample coffee powder 5 received therein. The temperature sensor 93 is connected to a contact 94 which is adapted to be brought into sliding contact with a contact 96 secured to the integrating sphere 22 when the sample container 3 held by the holder 4 occupies the measuring position.

As illustrated in FIG. 1, a temperature sensor 97 for detecting temperature within the measuring chamber 2 is attached to a central partition wall 98 defining the measuring chamber 2 within which the near-infrared spectrometer 10 is arranged. A temperature regulator 99 mounted to the central partition wall 98 is operative in response to a signal from the temperature sensor 97, to regulate the temperature within the measuring chamber 2, hence, various components of the near-infrared spectrometer 10 to a predetermined value.

A control chamber 101 is defined within the cabinet 1 by the central partition wall 98. An operation panel 102 is attached to a front wall of the control chamber 101. The operation panel 102 has arranged thereon a manual operation button 111 for manually operating the evaluating apparatus, an automatic operation button 112 for automatically operating the evaluating apparatus, a transmitted luminous-intensity selector button 113 for selecting the operation of only the luminous-intensity detecting element 28, a reflected and transmitted luminous-intensity selector button 114 for selecting the operation of the pair of luminous-intensity detecting elements 26 and 27 within the integrating sphere 22 in addition to the luminous-intensity detecting element 28, a start button 115 and a stop button 116.

The control chamber 101 has incorporated therein a control unit generally designated by the reference numeral 120, subsequently to be described in detail with reference to FIG. 6. The control unit 120 comprises an input-output-signal processing device 121, a memory device 122 connected thereto, and a calculation device 123 connected to the signal processing device 121 and the memory device 122. The input-output-signal processing device 121 is connected to various components of the aforementioned near-infrared spectrometer 10, the sample supply mechanism 30 and the transport means 60, and to the operation buttons 111 to 116. The memory device 122 has a RAM (Random Access Memory) which has stored and set therein content conversion coefficients, a temperature setting value, temperature correction values, operating procedures, characteristic coefficients, and appraisal coefficients. The characteristic coefficients and the appraisal coefficients are based on sensuous examination or the like.

The calculation device 123 calculates contents of various components such as protein, cane, sugar, chlorogenic acid, caffeine, resin, moisture and the like in the sample coffee powder 5, based on the signals from the luminous-intensity detecting elements 26, 27 and 28 of the near-infrared spectrometer 10, and the content conversion coefficients and the temperature correction values stored in the memory device 122. The component contents are stored in the RAM of the memory device 122.

The calculation device 123 also calculates characteristic values such as acidity, bitterness, sweetness, smell or aroma, and body, based on the signals from the luminous-intensity detecting elements 26, 27 and 28, and the characteristic coefficients and the temperature correction values stored in the RAM of the memory device 123. The characteristic values may be obtained on the basis of the calculated component contents. The calculated characteristic values are stored in the RAM of the memory device 122.

The calculation device 123 further calculates appraisal values on the basis of the signals from the luminous-intensity detecting elements 26, 27 and 28, and the appraisal coefficients and the temperature correction values stored in the RAM of the memory device 123. The appraisal values may be obtained on the basis of the calculated component contents. The calculated appraisal values are stored in the RAM of the memory device 122.

Connected to the input-output-signal processing device 121 are a display device 126 of LED or CRT type mounted to the operating panel 102, and a printer 127 incorporated in the control chamber 101. The display device 126 is composed of a display unit 126a for visually displaying the operating procedures of the evaluating apparatus, and a display unit 126b for visually displaying the results of the evaluation. The printer 127 prints out and displays the signals from the control unit 120.

The construction of the aforesaid control unit 120 will be described with reference to FIG. 6. Connected to the input side of the input-output-signal processing device 121 are the operation buttons 111 to 116, the luminous-intensity detecting elements 26, 27 and 28, the level sensor 36, the position sensors 81 and 82, the temperature sensors 93 and 97, and a keyboard 128. Connected to the output side of the input-output-signal processing device 121 through respective drive units 130 to 139 are the light source 11, the temperature regulator 99, the stepping motor 14, the solenoid actuator 35, the motor 43, the cleaners 46 to 49, the electromagnet 54, the motor 74, the solenoid actuator 87 and the nozzle 89.

Figure 7A:
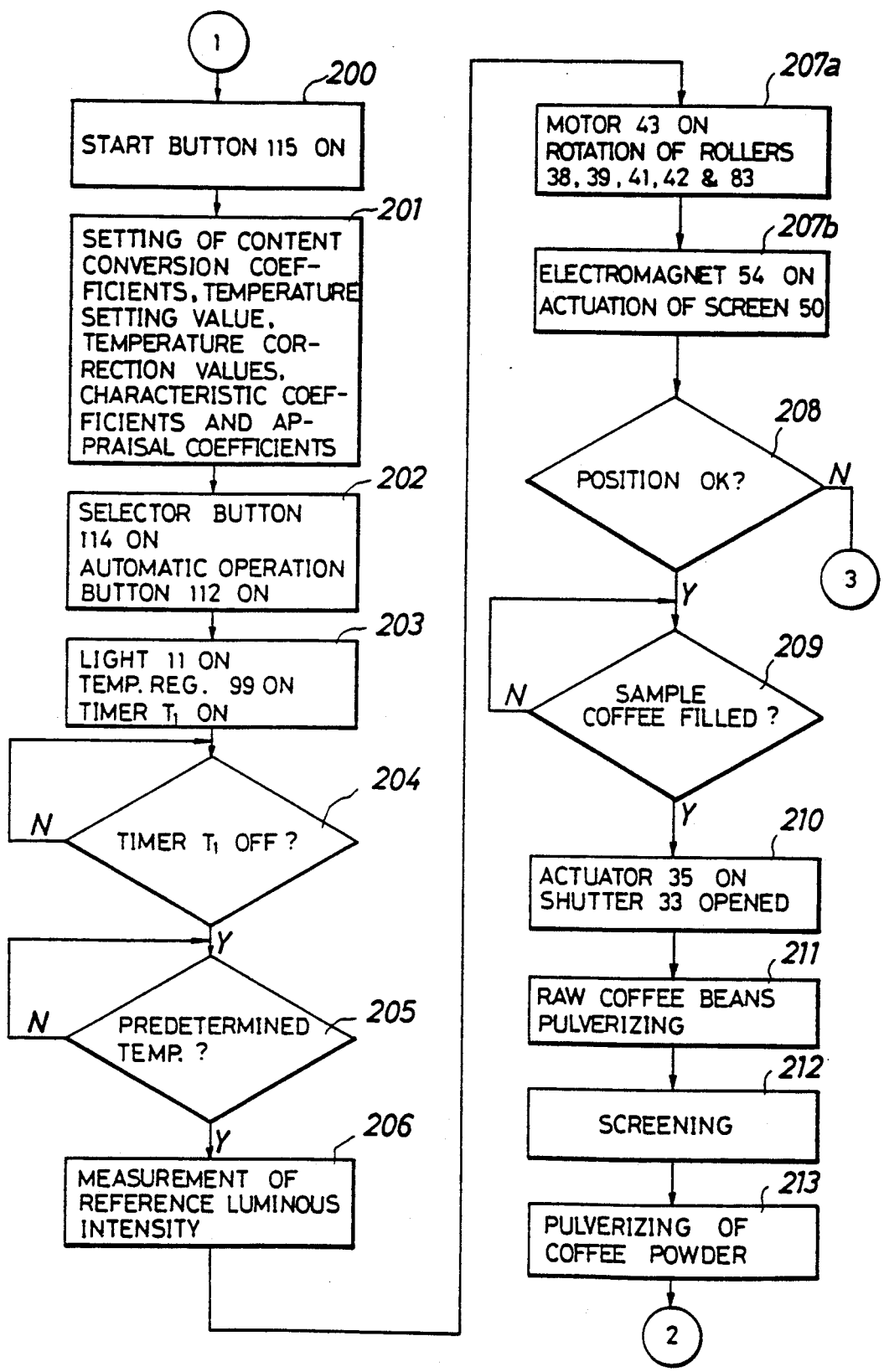
Figure 7B:
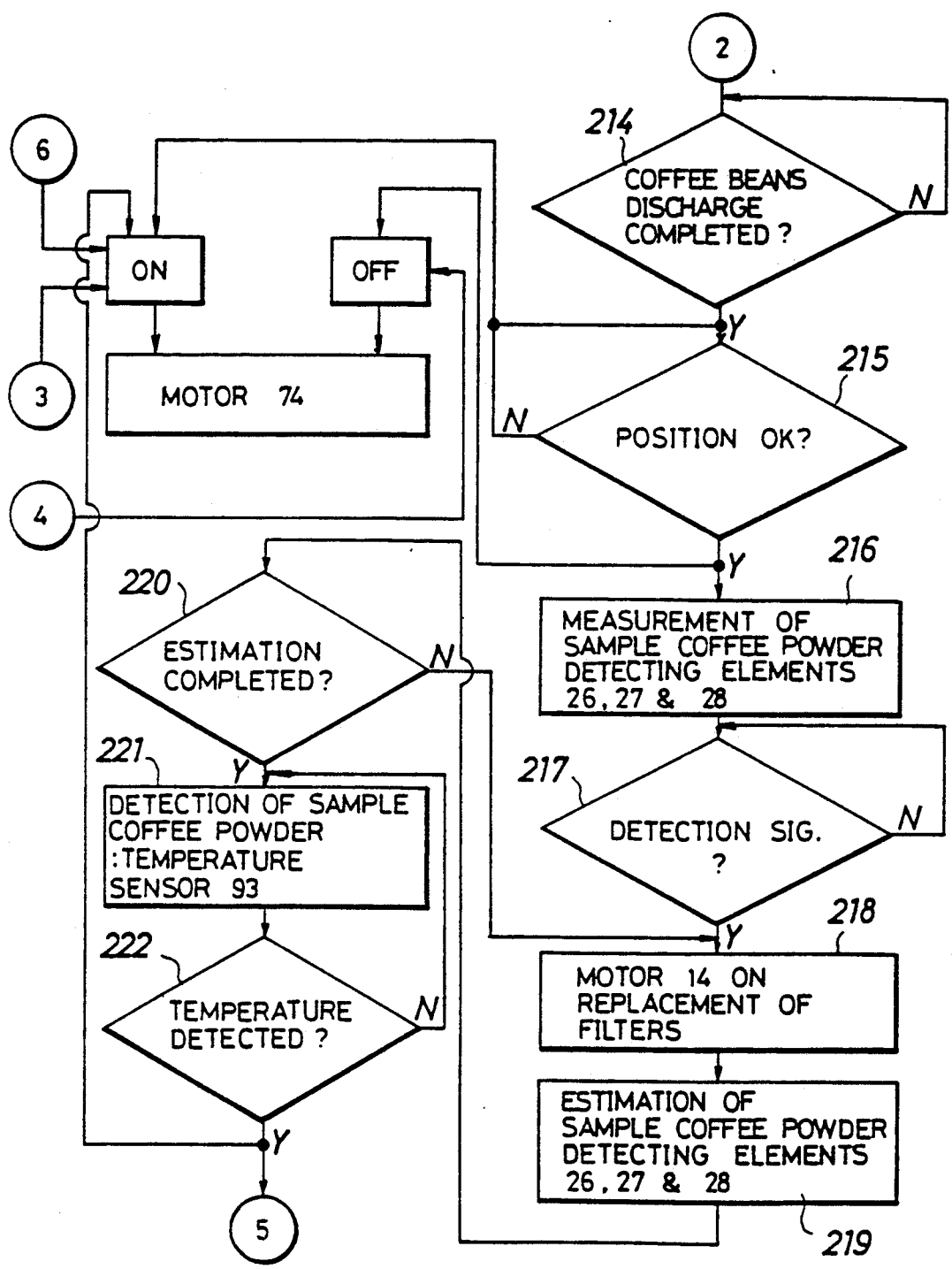

The operation of the evaluating apparatus constructed as set forth above will now be described with reference to the flow chart shown in FIGS. 7A through 7C. At a step 200, the start button 115 is depressed to turn on an electric power source. At a step 201, the keyboard 128 is operated to set and store the content conversion coefficients for calculating the contents of various components in the sample coffee powder, the temperature setting value, the temperature correction values, the characteristic coefficients, and the appraisal coefficients in the RAM of the memory device 122 of the control unit 120. The content conversion coefficients are previously obtained by a multiple regression analysis (or also called a hypercomplex regression analysis) on signal-processed values of the detecting signals from the luminous-intensity detecting elements 26, 27 and 28, based on component contents of a multiplicity of types of sample coffee powders measured by a chemical-quantitative analysis method such as iodine colorimetric method or iodometric electric current titration method.

The multiple regression analysis on contents of various components such as protein, resin, chlorogenic acid, caffeine, cane sugar and moisture, for example, in sample coffee powder will be described with reference to a case where ten optical filters whose respective nominal wavelengths are 1680 nm, 1818 nm, 1840 nm, 1904 nm, 1940 nm, 2100 nm, 2180 nm, 2190 nm, 2230 nm and 2310 nm, for example, are employed to conduct measurement or evaluation. In this case, the following linear relationship is satisfied:

$$
\begin{aligned}
C_{as} =\ & F_{a0} + F_{a(1680)} \cdot \log 1/R_{a(1680)} \\
& + F_{a(1818)} \cdot \log 1/R_{a(1818)} \\
& + \ldots \\
& + F_{a(2230)} \cdot \log 1/R_{a(2230)} \\
& + F_{a(2310)} \cdot \log 1/R_{a(2310)}
\end{aligned}
$$

where $C_{as}$ is contents of components in sample coffee powder in percentage;

$F_{a0}$ and $F_{a(1680)}$ to $F_{a(2310)}$ are content conversion coefficients stored in the memory device; and $\log 1/R_{a(1680)}$ to $\log 1/R_{a(2310)}$ are respective absorbances ($\log I_0/I$) measured by the use of ten optical filters.

For instance, the following relationships are obtained:

$$
\begin{aligned}
\text{Protein} =\ & 3.54 - 474.29 \cdot \log 1/R_{(1904)} \\
& + 301.05 \cdot \log 1/R_{(1940)} \\
& - 768.55 \cdot \log 1/R_{(2180)} \\
& + 805.35 \cdot \log 1/R_{(2190)} \\
& + 196.32 \cdot \log 1/R_{(2230)} \\
& - 98.05 \cdot \log 1/R_{(2310)}
\end{aligned}
$$

$$
\begin{aligned}
\text{Resin} =\ & 9.29 - 111.68 \cdot \log 1/R_{(1840)} \\
& - 220.51 \cdot \log 1/R_{(2180)} \\
& + 231.16 \cdot \log 1/R_{(2310)}
\end{aligned}
$$

$$
\begin{aligned}
\text{Moisture} =\ & 6.90 - 77.36 \cdot \log 1/R_{(1904)} \\
& + 85.15 \cdot \log 1/R_{(1940)} \\
& - 124.82 \cdot \log 1/R_{(2180)} \\
& + 124.05 \cdot \log 1/R_{(2230)} \\
& - 15.35 \cdot \log 1/R_{(2310)}
\end{aligned}
$$

$$
\begin{aligned}
\text{Cane Sugar} =\ & 19.93 + 74.33 \cdot \log 1/R_{(2100)} \\
& - 213.48 \cdot \log 1/R_{(2190)} \\
& + 88.63 \cdot \log 1/R_{(2310)}
\end{aligned}
$$

-continued $$\begin{aligned}
\text{Caffeine} = &\ 3.05 + 55.91 \cdot \log 1/R_{(1680)} \\
&+ 322.05 \cdot \log 1/R_{(1818)} \\
&- 426.97 \cdot \log 1/R_{(1840)} \\
&+ 167.84 \cdot \log 1/R_{(1904)} \\
&- 105.65 \cdot \log 1/R_{(1940)} \\
&- 4.46 \cdot \log 1/R_{(2310)}
\end{aligned}$$

$$\begin{aligned}
\text{Chrologenic Acid} = &\ -1.07 + 351.11 \cdot \log 1/R_{(1680)} \\
&- 513.34 \cdot \log 1/R_{(1840)} \\
&+ 49.61 \cdot \log 1/R_{(1904)} \\
&+ 126.37 \cdot \log 1/R_{(2100)} \\
&- 415.10 \cdot \log 1/R_{(2190)} \\
&- 374.09 \cdot \log 1/R_{(2230)}
\end{aligned}$$

The aforesaid values $F_{aO}$ and $F_{a(1680)}$ to $F_{a(2230)}$ are stored in the RAM of the memory device 122.

Absorption of the near-infrared light beam applied to the sample coffee powder, into the same is a phenomenon occurring due to vibration of the chains of atoms forming the molecules by thermal energy. Since the natural resonant frequency varies depending upon the kind of atoms and the chain conditions, the vibration changes in magnitude within the wavelength range of the near-infrared light beam, so that the thermal absorption occurs. In addition, if the initial thermal energy of the sample coffee powder is low, i.e., if the temperature thereof is low, the absorption amount due to the difference in the molecular structure cannot accurately be measured because the vibration is low in magnitude. Accordingly, it is necessary to correct the calculated results of the calculation device 123 in accordance with the temperature of the sample coffee powder to be evaluated. For instance, no correction is required for temperatures above 20° C. For a temperature of 10° C., however, an accurate or true value is obtained if 1.0% is added to the calculated results of the calculation device 123. The correction value changes generally linearly in a range of from 10° C. to 20° C.

The temperature setting value stored in the memory device 122 is utilized to regulate the temperature of various components of the near-infrared spectrometer 10, to a predetermined value, and is normally set to 25° C. The principal purpose of maintaining the temperature of the near-infrared spectrometer 10 to the predetermined value is to prevent variations in temperature of the sample coffee powder 5 in the sample container 3.

An example of a multiple regression analysis on the characteristic values will next be described. The characteristic values are obtained in the same manner as the component contents described above. It is apparent that various characteristic values such as acidity, bitterness, sweetness, smell or odor, and body depend upon the contents of components such as protein, cane sugar, resin, chlorogenic acid, caffeine and moisture. For instance, a tannin component centering around the chlorogenic acid of the coffee beans represents acidity and bitterness. In addition, the diketopiperazine or the like formed by the protein represents bitterness in the coffee. That is, the characteristic values are obtained on the basis of the signals from the luminous-intensity detecting elements 26, 27 and 28 and the characteristic coefficients stored in the RAM of the memory device 122.

The following relationship is satisfied on the characteristic values:

$$\begin{aligned}
C_{bs} = &\ F_{b0} + F_{b(1680)} \cdot \log 1/R_{b(1680)} \\
&+ F_{b(1818)} \cdot \log 1/R_{b(1818)} \\
&+ \ldots \\
&+ F_{b(2230)} \cdot \log 1/R_{b(2230)} \\
&+ F_{b(2310)} \cdot \log 1/R_{b(2310)}
\end{aligned}$$

where $C_{bs}$ is the characteristic values of the sample coffee powder;

$F_{b0}$ and $F_{b(1680)}$ to $F_{b(2310)}$ are characteristic coefficients stored in the memory device; and $\log 1/R_{b(1680)}$ to $\log 1/R_{b(2310)}$ are respective absorbances ($\log I_0/I$) measured by the use of ten optical filters.

The characteristic values vary dependent upon the variety of coffee beans and the national traits or nationality.

For example, the following relationships are obtained:

$$\begin{aligned}
\text{Acidity} = &\ 52.87 + 1252.89 \cdot \log 1/R_{b(1680)} \\
&+ 15869.55 \cdot \log 1/R_{b(1818)} \\
&- 17142.19 \cdot \log 1/R_{b(1840)} \\
&+ 2135.72 \cdot \log 1/R_{b(1904)} \\
&- 1465.16 \cdot \log 1/R_{b(1940)} \\
&- 1424.55 \cdot \log 1/R_{b(2100)} \\
&+ 19127.67 \cdot \log 1/R_{b(2180)} \\
&- 18561.75 \cdot \log 1/R_{b(2190)} \\
&+ 256.73 \cdot \log 1/R_{b(2230)} \\
&- 92.99 \cdot \log 1/R_{b(2310)}
\end{aligned}$$

$$\begin{aligned}
\text{Bitterness} = &\ -45.25 - 2603.25 \cdot \log 1/R_{b(1680)} \\
&+ 5426.65 \cdot \log 1/R_{b(1818)} \\
&- 1936.74 \cdot \log 1/R_{b(1840)} \\
&- 3477.97 \cdot \log 1/R_{b(1904)} \\
&+ 2078.69 \cdot \log 1/R_{b(1940)} \\
&- 488.10 \cdot \log 1/R_{b(2100)} \\
&+ 1741.46 \cdot \log 1/R_{b(2180)} \\
&- 3346.53 \cdot \log 1/R_{b(2190)} \\
&+ 3309.19 \cdot \log 1/R_{b(2230)} \\
&- 835.03 \cdot \log 1/R_{b(2310)}
\end{aligned}$$

$$\begin{aligned}
\text{Sweetness} = &\ -10.93 - 2833.73 \cdot \log 1/R_{b(1680)} \\
&+ 25257.41 \cdot \log 1/R_{b(1818)} \\
&- 21666.06 \cdot \log 1/R_{b(1840)} \\
&- 497.15 \cdot \log 1/R_{b(1904)} \\
&+ 218.40 \cdot \log 1/R_{b(1940)} \\
&- 2299.66 \cdot \log 1/R_{b(2100)} \\
&+ 25477.24 \cdot \log 1/R_{b(2180)} \\
&- 27578.05 \cdot \log 1/R_{b(2190)} \\
&+ 5492.53 \cdot \log 1/R_{b(2230)} \\
&- 1556.67 \cdot \log 1/R_{b(2310)}
\end{aligned}$$

$$
\begin{aligned}
\text{Aroma} = \ & 35.57 - 2847.43 \cdot \log 1/R_{b(1680)} \\
& + 28287.29 \cdot \log 1/R_{b(1818)} \\
& - 24269.84 \cdot \log 1/R_{b(1840)} \\
& + 1487.37 \cdot \log 1/R_{b(1904)} \\
& - 1268.91 \cdot \log 1/R_{b(1940)} \\
& - 2538.97 \cdot \log 1/R_{b(2100)} \\
& + 31070.15 \cdot \log 1/R_{b(2180)} \\
& - 32549.95 \cdot \log 1/R_{b(2190)} \\
& + 4770.64 \cdot \log 1/R_{b(2230)} \\
& - 1725.94 \cdot \log 1/R_{b(2310)}
\end{aligned}
$$

$$
\begin{aligned}
\text{Body} = \ & -20.92 - 576.47 \cdot \log 1/R_{b(1680)} \\
& + 17826.62 \cdot \log 1/R_{b(1818)} \\
& - 16732.58 \cdot \log 1/R_{b(1840)} \\
& + 318.25 \cdot \log 1/R_{b(1904)} \\
& - 405.04 \cdot \log 1/R_{b(1940)} \\
& - 430.64 \cdot \log 1/R_{b(2100)} \\
& + 11890.81 \cdot \log 1/R_{b(2180)} \\
& - 15503.44 \cdot \log 1/R_{b(2190)} \\
& + 5355.54 \cdot \log 1/R_{b(2230)} \\
& - 1390.99 \cdot \log 1/R_{b(2310)}
\end{aligned}
$$

The above values $C_{bs}$ are stored in the RAM of the memory device 122.

The appraisal values are obtained by the signals from the luminous-intensity detecting elements 26, 27 and 28 and the appraisal coefficients stored in the RAM of the memory device 122, in line with the following relationship:

$$
\begin{aligned}
C_{cs} = \ & F_{c0} + F_{c(1680)} \cdot \log 1/R_{c(1680)} \\
& + F_{c(1818)} \cdot \log 1/R_{c(1818)} \\
& + \ldots \\
& + F_{c(2230)} \cdot \log 1/R_{c(2230)} \\
& + F_{c(2310)} \cdot \log 1/R_{c(2310)}
\end{aligned}
$$

where $C_{cs}$ is the appraisal values of the sample coffee powder;

$F_{c0}$ and $F_{c(1680)}$ to $F_{c(2310)}$ are the appraisal coefficients stored in the memory device; and $\log 1/R_{c(1680)}$ to $\log 1/R_{c(2310)}$ are respective absorbances ($\log I_O/I$) measured by the use of ten optical filters.

For instance, the appraisal values are obtained by the following relationship:

$$
\begin{aligned}
C_{cs} = \ & 136.28 - 2399.67 \cdot \log 1/R_{c(1680)} \\
& + 32095.46 \cdot \log 1/R_{c(1818)} \\
& - 28180.80 \cdot \log 1/R_{c(1840)} \\
& + 901.49 \cdot \log 1/R_{c(1904)} \\
& - 641.99 \cdot \log 1/R_{c(1940)} \\
& - 3429.75 \cdot \log 1/R_{c(2100)} \\
& + 36918.80 \cdot \log 1/R_{c(2180)} \\
& - 36616.79 \cdot \log 1/R_{c(2190)} \\
& + 2925.40 \cdot \log 1/R_{c(2230)} \\
& - 1490.20 \cdot \log 1/R_{c(2310)}
\end{aligned}
$$

the above value $C_{cs}$ is stored in the RAM of the memory device 122.

Now, as the reflected and transmitted luminous-intesity selector button 114 and the automatic operation button 112 are depressed at a step 202, the near-infrared spectrometer 10 is energized. At a step 203, the input-output-signal processing device 121 sends an ON signal to the drive unit 130 to turn on the light source 11. A timer $T_1$ incorporated in the input-output-signal processing device 121 is also turned on. The timer $T_1$ sets a period of time for which the near-infrared monochromatic light of the specific wavelength based on the light from the light source 11 stabilizes. At the step 203, an ON signal is sent to the drive unit 131 to actuate the temperature regulator 99 for maintaining the various components of the near-infrared spectrometer 10 to the predetermined value. At a step 204, as the time period set by the timer $T_1$ elapses, the input-output-signal processing device 121 causes the program to proceed to a step 205 where the temperature sensor 97 detects whether or not the near-infrared spectrometer 10 is brought to the temperature setting value stored in the memory device 122. In response to the signal from the temperature sensor 97 indicating that the near-infrared spectrometer 10 is brought to the predetermined temperature, the program proceeds to a step 206 where the measurement of the reference luminous intensities $I_O$ is carried out. The measurement of the reference luminous intensities subsequently to be described in detail, will be described here briefly.

Firstly, a reference plate is carried onto the sample container 3 filled with no sample coffee powder. The light source 11 applies the light to the reference plate through one of the ten optical filters 13a to 13j and through the transparent plate 25 of the integrating sphere 22. The light reflected by the reference plate and further reflected by the inner wall surface of the integrating sphere 22 is received by the luminous-intensity detecting elements 26 and 27 thereby measuring luminous intensity of the light, i.e., reflected reference luminous intensity. Similar measurements are performed through the remaining respective optical filters. In this manner, the reflected reference luminous intensities are measured which correspond respectively to the optical filters, and are stored in the memory device 122 of the control unit 120. Subsequently, the reference plate is removed out of the sample container 3. The light from the light source 11 is transmitted through the transparent plate 25 of the integrating sphere 22 and the transparent bottom wall of the sample container 3, and is received by the luminous-intensity detecting element 28 thereby measuring luminous intensity of the transmitted light, i.e., transmitted luminous intensity. The transmitted reference luminous intensities are measured through the respective optical filters 13a to 13j. In this manner, the transmitted reference luminous intensities are measured and are stored in the memory device 122. The manner of measuring the reference luminous intensities is not limited to that described above, but various other ways can be used to measure the reference luminous intensities.

Subsequent to the measurement of the luminous intensities $I_O$, the program proceeds to a step 207a where the input-output-signal processing device 121 sends an ON signal to the drive unit 134 to turn on the motor 43, to thereby rotate the rollers 38, 39, 41 and 42 as well as the roller 83. At a subsequent step 207b, the input-output-signal processing device 121 sends an ON signal to the drive unit 136 to energize the electromagnet 54, thereby actuating the vibratory screening device 50 so that the vibratory frame 51 is oscillated. At a step 208, the position sensor 81 detects whether or not the sample container 3 is located at the predetermined filling position. As the position sensor 81 detects that the sample container 3 is not located at the filling position, the input-output-signal processing device 121 sends an ON signal to the drive unit 137 to turn on the motor 74, to thereby move the holder 4 having held thereon the sample container 3, along the guide rail 64.

As the position sensor 81 detects that the sample container 3 is located at the filling position, the program proceeds to a step 209 where the level sensor 36 detects whether or not the raw coffee beans are received in the hopper 31. If the detection is affirmative, the program proceeds to a step 210 where the solenoid actuator 35 is turned on by the drive unit 133 to open the shutter 33, so that the raw coffee beans are fed toward the nip between the first pair of coarse grinding rollers 38 and 39 through the discharge port 32 of the hopper 31. The program proceeds to a step 211 where the coffee beans from the hopper 31 are pulverized by the first pair of coarse grinding rollers 38 and 39, and is further pulverized finely by the second pair of fine grinding rollers 41 and 42. Pulverizing of the coffee beans by the first and second pairs of grinding rollers in the two step manner allows the pulverized coffee-bean particles to be sufficiently mixed with each other, to thereby enhance the measurement or evaluation accuracy.

At a subsequent step 212, the pulverized coffee powder falls onto the vibratory screen 52 and are sorted thereby. At a step 213, sample coffee powder 5 to be evaluated of a desired particle size having passed through the meshes of the screen 52 falls into the sample container 3 located at the filling position, and is filled therein. Coffee powder overflowing from the sample container 3 falls into the container 58. Thus, a predetermined amount of sample coffee powder 5 is filled in the sample container 5. In addition, the relatively coarse pulverized powder falls into the container 58 through the discharge chute 57.

At a step 214, the level sensor 36 detects whether or not the coffee beans within the hopper 31 are completely discharged therefrom through the discharge port 32. If the detection is affirmative, the input-output-signal processing device 121 sends an ON signal to the drive unit 137 in response to the signal from the level sensor 36, to actuate the reversible motor 74. This causes the holder 4 having held thereon the sample container 3 to be moved toward the measuring position along the guide rail 64. When the holder 4 moves from the filling position toward the measuring position, the sample coffee powder 5 standing up above the rim of the sample container 3 held by the holder 4 is compressed by the rotating roller 83 so that the sample coffee powder 5 is filled under pressure into the sample container 3, and the upper surface of the sample coffee powder 5 within the sample container 3 is flattened. At this time, the coffee powder overflowing from the sample container 3 falls into the container 58. At a step 215, the position sensor 82 detects whether or not the sample container 3 held by the holder 4 reaches the predetermined measuring position. If the detection is affirmative, an OFF signal sent to the drive unit 137 causes the motor 74 to stop in operation. The program proceeds to a step 216 where the measurement or evaluation by the near-infrared spectrometer 10 is started in response to the affirmative signal from the position sensor 82.

At the outset, the motor 14 is turned on by the drive unit 132 to align selected one of the optical filters 13a to 13j, which has a desired nominal wavelength, with the optical axis of the light from the light source 11. The light from the light source 11 becomes the near-infrared monochromatic light beam having the specific wavelength after having passed through the selected optical filter such as one designated by the reference numeral 13a. Subsequently, the light passes through the slit member 21 and the light intake window 23 of the integrating sphere 22, and enters the same. The light having entered the integrating sphere 22 is applied vertically to the sample coffee powder 5 within the sample container 3. Luminous intensity of the light transmitted through the sample coffee powder 5 is detected by the luminous-intensity detecting element 28, and the signal therefrom is sent to the input-output-signal processing device 121. Luminous intensity of the light reflected by the sample coffee powder 5 and then reflected by the inner wall surface of the integrating sphere 22 is detected by the pair of luminous-intensity detecting elements 26 and 27, and the signals therefrom are also sent to the input-output-signal processing device 121.

If it is desired to effect the evaluation through a plurality of wavelengths, the input-output-signal processing device 121 is operative, at a step 217, in response to the signals from the luminous-intensity detecting elements 26, 27 and 28, to cause the program to proceed to a step 218 where the motor 14 is turned on by the drive unit 132. The filter assembly 13 is angularly moved about the axis thereof by the motor 14 in such a manner that the optical filters 13b to 13j are successively aligned with the optical axis of the light from the light source 11. Luminous intensity detection similar to that effected through the filter 13a is successively performed, at a step 219, by the luminous-intensity detecting elements 26, 27, and 28 through the respective filters 13b to 13j. Signals from the elements 26, 27 and 28 are successively sent to the input-output-signal processing device 121. Each of the filters 13a to 13j has a half-width in a wavelength range of ±10 nm in the corresponding specific wavelength. The input-output-signal processing device 121 judges, at a step 220, whether or not the detection is completed through the respective filters 13a to 13j. If the detection is not completed through all of the filters 13a to 13j, the program is returned to the step 218.

As the detection is completed through all of the filters 13a to 13j, the program proceeds to a step 221 where the temperature sensor 93 detects the temperature of the sample coffee powder 5 within the sample container 3, and a signal representative of the temperature is sent to the input-output-signal processing device 121. At a step 222, the signal processing device 121 judges whether or not the temperature detection is conducted by the temperature sensor 93. If the judgment is affirmative, the input-output-signal processing device 121 turns on a timer $T_2$ incorporated therein at a step 223, and sends an ON signal to the drive unit 135 to actuate the cleaning devices 46 through 49, thereby cleaning the rollers 38, 39, 41 and 42.

Moreover, the input-output-signal processing device 121 sends an ON signal to the drive unit 137 to actuate the motor 74, to thereby move the holder 4 having held thereon the sample container 3, toward the filling position. As the position sensor 81 detects, at a step 224, that the sample container 3 reaches the predetermined filling position, the input-output-signal processing device 121 sends an OFF signal to the drive unit 137 to stop the operation of the motor 74. When the holder 4 is moved toward the filling position, the first cleaner 84a is brought into sliding contact with the lower surface of the transparent plate 25 closing the measuring window 24 of the integrating sphere 22 to clean the transparent plate 25. In addition, the second cleaner 84b is brought into sliding contact with the surface of the luminous-intensity detecting element 28 fixedly mounted on the support rod 29 to clean the element 28. Furthermore, the third cleaner 85 fixedly mounted on the support rod 29 is brought into sliding contact with the transparent bottom wall of the sample container 3 to clean the same.

As the predetermined period of time set by the timer $T_2$ elapses at a step 225, the input-output-signal processing device 121 sends, at a step 226, an OFF signal to the drive unit 135 to stop the operation of the cleaning devices 46 through 49. At a subsequent step 227, the input-output-signal processing device 121 sends an OFF signal to the drive unit 133 to stop the operation of the solenoid actuator 35. This causes the shutter 33 to be moved to close the discharge port 32 of the hopper 31. As the position sensor 81 detects, at the aforementioned step 224, that the sample container 3 reaches the predetermined filling position, the input-output-signal processing device 121 sends an ON signal to the drive unit 138 to actuate the solenoid actuator 87. The bracket 76 having carried thereon the motor 74 is angularly moved by the actuator 87 about the axis of the guide rail 64 through 90°. At this time, the sample coffee powder 5 within the sample container 3 falls therefrom into the container 58.

At a subsequent step 229, the input-output-signal processing device 121 turns on a timer $T_3$ incorporated therein, and sends an ON signal to the drive unit 139 to actuate the nozzle 89. Compressed air is blown through the nozzle 89 against the sample container 3 having angularly moved through 90°, to blow off the sample coffee powder 5 from the sample container 3 to clean the interior thereof. As the period of time set by the timer $T_3$ elapses at a step 230, the input-output-signal processing device 121 sends an OFF signal to the drive unit 139 to stop the operation of the nozzle 89. At a step 232, an OFF signal is sent to the drive unit 138 to stop the operation of the solenoid actuator 87. The holder 4 located at the filling position is angularly moved through 90° to the initial position about the axis of the guide rail 64, to prepare for a subsequent evaluation of sample coffee powder.

As mentioned previously, the detecting signals from the luminous-intensity detecting elements 26, 27 and 28 and the detecting signal from the temperature sensor 93 are sent to the input-output-signal processing device 121. At a step 233, the calculation device 123 of the control unit 120 calculates the contents of protein, resin, chlorgenic acid, caffeine, cane sugar and moisture, based on the detecting signals from the luminous-intensity detecting elements 26, 27 and 28, and the content conversion coefficients for the coffee components and the temperature correction values stored in the RAM of the memory device 122. Further, the characteristic values and the appraisal values are calculated. The calculated component contents, characteristic values and appraisal values are stored in the RAM of the memory device 122. In addition, the calculated component contents, characteristic values and appraisal values are digitally displayed on the display unit 126b of the operation panel 102, and are automatically printed out and displayed by the printer 127 at a step 235. If it is desired to stop the operation of the evaluation apparatus, the stop button 116 is depressed.

A case will next be described where, in place of depression of the automatic operation button 112, the manual operation button 111 is depressed to manually operate the evaluating apparatus. In this connection, raw coffee beans, which are dried to have their moisture content equal to or less than 10% and from which endocarp is removed, are brittle or frangible as a whole and low in pulverizing efficiency, depending upon the physical property of the raw coffee beans if they are pulverized by a rotary shock pulverizer. Temperature rise in the raw coffee beans is so high that there is possibility that a bad effect or influence is exerted on the raw coffee beans. Accordingly, the raw coffee beans are first pulverized coarsely by a pair of pulverizing rollers, and are then finely pulverized by the rotary shock pulverizer. By doing so, there can effectively be obtained sample coffee powder which is uniform in grain size.

Figure 8:
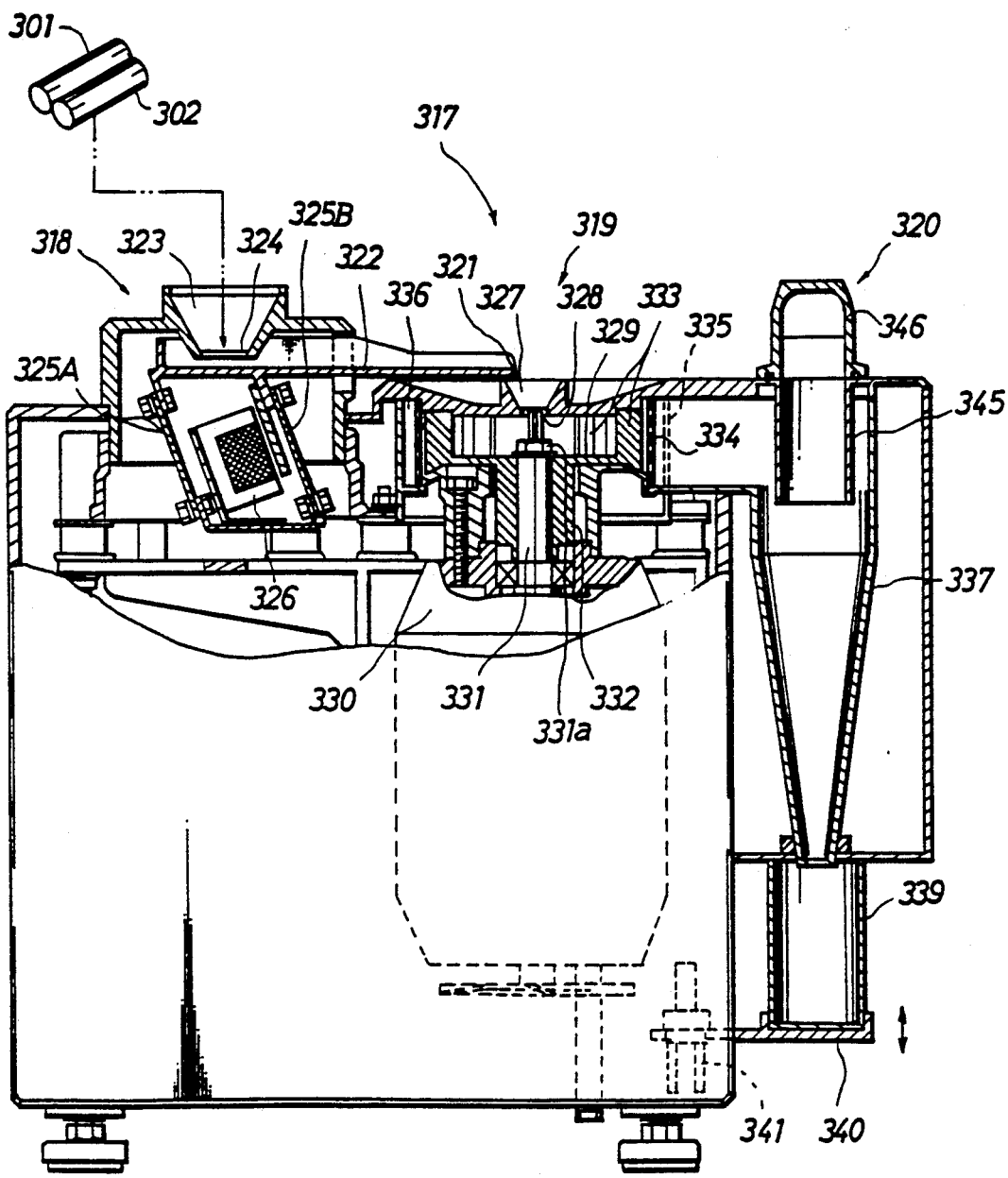
FIG. 8 is a partially broken-away, front elevational view of a sample pulverizing equipment.
Figure 9:
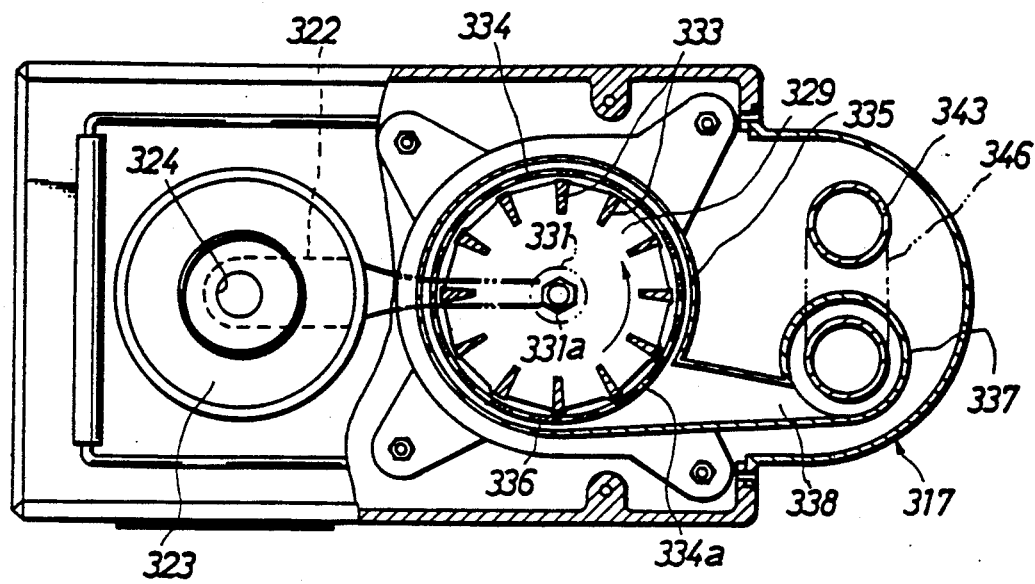
FIG. 9 is a partially broken-away, top plan view of the sample pulverizing equipment shown in FIG. 8.
Figure 10:
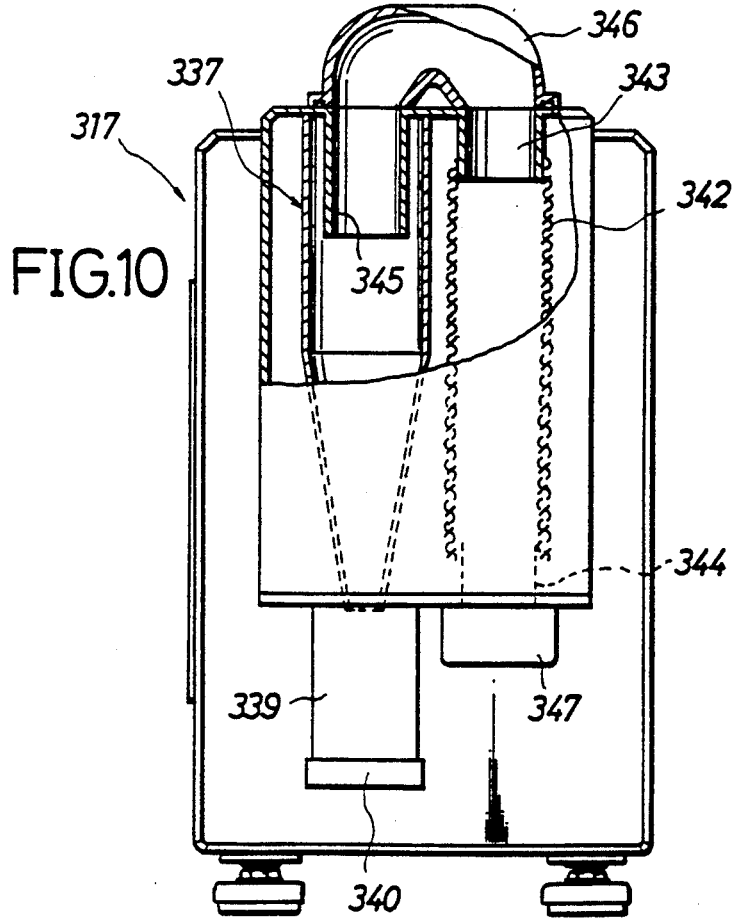
FIG. 10 is a right-hand side elevational view of the sample pulverizing equipment shown in FIG. 8.

Specifically, referring to FIGS. 8 through 10, raw coffee beans, which are dried to have their moisture content equal to or less than 10% and from which endocarp is removed, are first passed through a pair of coarse grinding rollers 301 and 302 rotatably arranged in opposite relation to each other, to form coarse powder. Subsequently, the coarse powder is further pulverized finely by a rotary shock pulverizer or a centrifugal sample pulverizing equipment 317 which is composed of a constant-quantity supply section 318, a pulverizing section 319 and a separating section 320. The constant-quantity supply section 318 in this embodiment consists of a so-called vibratory supply unit. That is, the constant-quantity supply section 318 has a supply chute 322 whose one end opens to form a discharge portion 321. The supply chute 322 is arranged horizontally, and a bottom of the supply chute 322 at the other end thereof is located adjacent a falling port 324 at a lower end of a throwing hopper 323. The other end of the supply chute 322 is so formed as to be supported by leaf springs 325A and 325B, and to be oscillated by a vibrator 326.

The pulverizing section 319 has a supply hopper 327 whose lower end is formed into a supply port 328 located below the discharge portion 321 of the supply chute 322. A pulverizing disc 329 having a substantially circular upper face located below the supply hopper 327. At a lower center of the pulverizing disc 329, a boss or a hub 332 is formed into which a shaft 331 of a commutator motor 330 located below the pulverizing disc 329 is fitted. On the other hand, a plurality of, i.e., twelve in the embodiment, pulverizing vanes or blades 333 are arranged vertically in equidistantly spaced relation to each other at the outer periphery of the upper face of the pulverizing disc 329. The pulverizing blades 333 rotate at high speed together with the pulverizing disc 329 by driving of the motor 330. A screw 331a is utilized to fasten the pulverizing disc 329 to the shaft 331.

At the outer periphery of the pulverizing disc 329, a cylindrical perforated ring 334 is arranged through a slight gap between the perforated ring 334 and the pulverizing blades 333. A plurality of perforations 334a are formed in the perforated ring 334. Each perforation 334a has a dimension which is selected dependent upon the dimension of the desirable sample coffee powder. In this embodiment, the dimension of each perforation 334a is 50 $\mu$m. Moreover, an outer peripheral ring 335 is arranged about the periphery of the perforated ring 334 to form a pulverulent collecting passage 336 between the outer peripheral ring 335 and the perforated ring 334.

The separating section 320 consists primarily of a cyclone separator 337. That is, the pulverulent collecting passage 336 and the cyclone separator 337 are connected to each other tangentially through a communication passage 338. The cyclone separator 337 has a lower end which sealingly faces toward a sample bottle 339. The sample bottle 339 is set on a resting table 340 which is movable vertically under the influence of a coiled spring 341.

In the vicinity of the cyclone separator 337, a tubular filter 342 made of cloth or the like is arranged which extends between upper and lower rings 343 and 344. An inner tube 345 and the upper ring 343 of the cyclone separator 337 are connected to each other through a U-shaped connecting pipe 346. Further, a dust collector 347 connected to the lower end of the lower ring 344 is arranged detachably and sealingly.

In a case where the sample pulverizing equipment 317 is utilized, the vibrator 326 thereof is operated, and coffee powder coarsely pulverized by the pair of coarse grinding rollers 301 and 302 is fed into the feed hopper 323. Then, the coffee powder in the vicinity of the falling port 324 is conveyed toward the discharge portion 321 through the supply chute 322 oscillated by the vibrator 326, by an appropriate amount. The coffee powder falls into the supply hopper 327 successively through the discharge portion 321. The coffee powder is then supplied onto the pulverizing disc 329 through the supply port 328.

The pulverizing disc 329 rotates at high speed, i.e., at or above 10,000 rpm by the commutator motor 330. The coffee powder supplied onto the pulverizing disc 329 is scattered and blown off toward the perforated ring 334 by centrifugal force. The coffee powder is then smashed under impact and shearing force of the pulverizing blades 333 rotating at high speed, and are pulverized into fine sample coffee powder. Sample coffee powder pulverized smaller than the perforations 334a of the perforated ring 334 escapes into the powder collecting passage 336 through the perforations 334a.

By the way, the pulverizing blades 333 rotating at high speed create or cause moving air or wind by which the pulverized sample coffee powder is promoted to leak from the perforations 334a of the perforated ring 334. Further, the moving air transports the sample coffee powder within the powder collecting passage 336, into the cyclone separator 337 through the communication passage 338.

The moving air together with the sample coffee powder, conveyed into the cyclone separator 337, flows down like volute through the conical section of the separator 337. The sample coffee powder stalled falls down into the sample bottle 339 from the lower end of the conical section. On the other hand, coffee powder smaller than that mentioned above, for example, of the order of 20 $\mu$m or less, and the dust reach the tubular filter 342, together with the moving air, through the inner tube 345, the connecting pipe 346 and the upper ring 343. The coffee powder is filtered by the filter 342, and only the moving air flows outside of the filter 342. The coffee powder and dust extremely fine and inadequate for desired sample fall into the dust collector 347 from the lower ring 344. Air passing through the filter 342 is discharged outside of the pulverizing equipment 317.

The sample coffee powder uniformized to a predetermined size, as described above, is filled in the sample container 3 in a predetermined amount, and an upper surface of the sample coffee powder 5 in the sample container 3 is flattened. The sample container 3 filled with the sample coffee powder 5 is inserted into the cabinet 1 toward the measuring position, through the cover 78 and the opening 77. That is, as illustrated in FIG. 1, the turning handle 71 is pushed slightly into the cabinet 1. The push button 71b at the proximal end of the turning handle 71 is operated to cause the latch 71a at the distal end of the turning handle 71 to engage with the hook 9 on the holder 4. Subsequently, an operator pushes the holder 4 together with the turning handle 71 toward the measuring position, to move the holder 4 having held thereon the sample container 3 from the filling position to the measuring position. Then, the cover 78 shown in FIG. 5 is removed to open the opening 77. The operator clamps the grip 7 of the sample container 3 to dismount the same from the holder 4, and takes the sample container 3 out of the cabinet 1 through the opening 77. The top surface of the sample coffee powder filled in the sample container 3 is flattened.

Subsequently, the sample container 3 is put into the measuring chamber 101 through the opening 77, and the projections 8 on the sample container 3 are fitted respectively into the guide grooves in the holder 4. Thus, the sample container 3 is mounted on the holder 4 located at the measuring position. The cover 78 is then fitted in the opening 77 to close the same. Subsequently, the near-infrared spectrometer 10 is operated to carry out measurement or evaluation. After completion of the evaluation, the turning handle 71 is pulled to move the holder 4 from the measuring position to the filling position. Once the holder 4 is located at the filling position, the turning handle 71 is turned to angularly move the holder 4, to allow the sample coffee powder within the sample container 3 held by the holder 4 to fall into the container 58. Subsequently, the latch 71a at the distal end of the turning handle 71 is disengaged from the hook 9 on the holder 4. It is of course that the sample container 3 may be taken out of the cabinet 1 through the opening 77 after the evaluation, to throw away the sample coffee powder to any desired location.

In order to obtain accurate detecting values of the contents, the sample coffee powder 5 to be filled in the sample container 3 is required to have a low particle size. The particle size should be 500 $\mu$m or less, preferably, approximately 50 $\mu$m. It it desirable that the measurement accuracy is $\pm 0.5\%$ or less. Accordingly, it is necessary to employ the screen 52 of the screening device 50 for sorting the pulverized sample coffee powder, which screen has the meshes less than 500 μm. Likewise, also in case where sample coffee beans are pulverized by the external pulverizing equipment 317 which is not incorporated in the evaluation apparatus shown in FIG. 1, the evaluating accuracy can be ensured if the pulverized sample coffee powder is screened and only the sample coffee powder having the particle size less than 500 μm is filled in the sample container 3. The reason for this is that as the size of the starch molecules is approximately 10 μm, the starch molecules do not uniformly appear on the upper surface of the sample container unless the sample coffee powder is pulverized to have the particle size less than 500 μm and, therefore, the vibration of the molecules due to the near-infrared light beam is not performed accurately.

As described previously, the crossing angle between selected one of the ten filters 13a to 13j of the filter assembly 13 and the optical axis of the illuminating light from the light source 11 can be adjusted to any desired value by the operation of the motor 14 in response to the signal from the input-output-signal processing device 121 of the control unit 120. Although it is basic or fundamental that the selected filter be used at such a position that its face is perpendicular to the optical axis of the illuminating light, it is possible to slide the transmitted nominal wavelength of the selected filter through an optional wavelength by changing the crossing angle of the filter to the optical axis of the illuminating light. The wavelength transmitted when the selected filter has its face perpendicular to the optical axis of the illuminating light is different from that when the selected filter has its face intersecting the optical axis at any angles other than 90°. As the crossing angle becomes smaller than 90°, the transmitted nominal wavelength slides toward the short wavelength. Within a near-infrared light beam range of from 1100 nm to 2500 nm, the effective transmitted nominal wavelength usually slides by several tens nanometers such as, for example, 70 nm, if the filter's face shifts from 90° with respect to the optical axis of the illuminated light. Accordingly, the crossing angle of the selected filter's face with respect to the optical axis of the illuminating light can be adjusted substantially continuously in order to enable continuous measurement or evaluation within the range of from 1100 nm to 2500 nm.

Although the embodiment illustrated in FIG. 1 employs ten filters 13a to 13j, it is needless to say that the evaluation may be effected by the use of a single filter. In this case, the incident angle of the light from the light source to the single filter may be fixed or variable.

Although the embodiment has been described, for convenience, as having the evaluation carried out based on the detecting signals from the luminous-intensity detecting elements 26 and 27 as well as the luminous-intensity detecting element 28, only the elements 26 and 27 may be employed, or only the element 28 may be employed. In the latter case, the transmitted luminous-intensity selector button 113 is depressed to conduct the evaluation. In addition, an external temperature sensor for detecting temperature of the exterior of the cabinet 1 may be substituted for the temperature sensor 97 for detecting the temperature within the measuring chamber 2. In this case, the temperature regulator 99 is operated in response to a signal from the external temperature sensor.

Although the embodiment has been described as having the content conversion coefficients, the temperature setting value, the temperature correction values, the characteristic coefficients and the appraisal coefficients inputted by the keyboard 128, the keyboard 128 is not necessarily required, if these values or coefficients are previously stored in a ROM (Read Only Memory) within the memory device 122. Further, the printer 127 need not be limited to the illustrated built-in type, but may be of externally connectable type. Moreover, although the embodiment has been described as having the pair of luminous-intensity detecting elements 26 and 27 arranged within the integrating sphere 22 for the purposes of enabling the compensation for the optical symmetry and facilitating efficient receiving of the reflected light from the sample coffee powder 5, the number of the elements need not be limited to two, but one or three or more elements may be arranged within the integrating sphere 22. Furthermore, the evaluation accuracy can further be ensured, if the detection of luminous intensity of the reflected light and the transmitted light is repeated in several times with respect to each of the optical filters 13a to 13j of the optical filter assembly 13 and the average value is taken.

What is claimed is:

1. A method for evaluating the quality of raw coffee beans, said method comprising:
   pulverizing raw coffee beans to form a sample coffee powder;
   applying near-infrared light of a predetermined wavelength to said sample coffee powder;
   detecting at least one of luminous intensity of light reflected from said sample coffee powder, or luminous intensity of light transmitted through said sample coffee powder;
   generating a signal derived from luminous intensity of light detected in step; and
   calculating at least one of characteristic values based on stored characteristic coefficients and said signal derived from the detected luminous intensity, or appraisal values based on stored appraisal values of said raw coffee beans and said signal derived from the detected luminous intensity.

2. The method according to claim 1, wherein both luminous intensity of light reflected from said sample coffee powder and luminous intensity of light transmitted through said sample coffee powder are detected.

3. The method according to claim 1, wherein both characteristic values and appraisal values are calculated.

4. The method according to claim 1, wherein step comprises a first pulverization step, wherein the raw coffee beans are pulverized to form a coarse powder, and a second pulverization step, wherein said coarse powder is pulverized to form said sample coffee powder.

5. The method according to claim 1, wherein pulverization of the raw coffee beans forms a sample coffee powder having a uniform grain size.

6. The method according to claim 1, further comprising drying said raw coffee beans to reduce their moisture content to a maximum of approximately 10% prior to pulverization.

7. The method according to claim 1, further comprising removing endocarps of said raw coffee beans prior to pulverization.

8. The method according to claim 1, wherein the predetermined wavelength of light applied to said sample coffee powder is within a range of from 1100 nm to 2500 nm.

9. The method according to claim 1 comprising the following steps:

pulverizing raw coffee beans to form a sample coffee powder;

applying near-infrared light of a first predetermined wavelength to said sample coffee powder;

detecting at least one of luminous intensity of light reflected from said sample coffee powder, or luminous intensity of light transmitted through said sample coffee powder, for said first predetermined wavelength;

generating a signal derived from luminous intensity of light detected in step;

applying near-infrared light of a second predetermined wavelength to said sample coffee powder;

detecting at least one of luminous intensity of light reflected from said sample coffee powder, or luminous intensity of light transmitted through said sample coffee powder, for said second predetermined wavelength;

generating a signal derived from luminous intensity of light detected in step; and calculating at least one of characteristic values based on stored characteristic coefficients and said signal derived from the detected luminous intensity for both said first and second predetermined wavelengths, or appraisal values based on stored appraisal values of said raw coffee beans and said signal derived from the detected luminous intensity for both said first and second predetermined wavelengths.

10. The method according to claim 9, wherein both luminous intensity of light reflected from said coffee powder and luminous intensity of light transmitted through said sample coffee powder are detected for both first and second predetermined wavelengths.

11. The method according to claim 9, wherein both characteristic values and appraisal values are calculated.

12. The method according to claim 9, wherein step comprises a first pulverization step, wherein the raw coffee beans are pulverized to form a coarse powder, and a second pulverization step, wherein said coarse powder is pulverized to from said sample coffee powder.

13. The method according to claim 9, wherein pulverization of the raw coffee beans forms a sample coffee powder having a uniform grain size.

14. The method according to claim 9, further comprising drying said raw coffee beans to reduce their moisture content to a maximum of approximately 10% prior to pulverization.

15. The method according to claim 14, further comprising removing endocarps of said raw coffee beans prior to pulverization.

16. The method according to claim 9, wherein each of said first and second predetermined wavelengths of light applied to said sample coffee powder is within a range of from 1100 nm to 2500 nm.

* * * * *